US010213551B2

(12) United States Patent
Voigt et al.

(10) Patent No.: US 10,213,551 B2
(45) Date of Patent: Feb. 26, 2019

(54) ALGORITHM FOR REMOVAL OF NOISE DURING ADMINISTRATION OF FLUID TO A PATIENT

(71) Applicants: Richard B. Voigt, Texas City, TX (US); George C. Kramer, Galveston, TX (US); Jordan Wolf, Santa Fe, TX (US)

(72) Inventors: Richard B. Voigt, Texas City, TX (US); George C. Kramer, Galveston, TX (US); Jordan Wolf, Santa Fe, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 342 days.

(21) Appl. No.: 14/963,031

(22) Filed: Dec. 8, 2015

(65) Prior Publication Data
US 2016/0158442 A1 Jun. 9, 2016

Related U.S. Application Data

(60) Provisional application No. 62/089,728, filed on Dec. 9, 2014.

(51) Int. Cl.
*A61M 5/172* (2006.01)
*A61M 5/168* (2006.01)

(52) U.S. Cl.
CPC ...... *A61M 5/1723* (2013.01); *A61M 5/16895* (2013.01); *A61M 2205/50* (2013.01); *A61M 2205/502* (2013.01); *A61M 2230/00* (2013.01)

(58) Field of Classification Search
CPC ............ A61M 5/1723; A61M 5/16895; A61M 2205/502; A61M 2205/50; A61M 2230/00
See application file for complete search history.

(56) References Cited

U.S. PATENT DOCUMENTS 4,650,464 A * 3/1987 Ruiz ..................... A61M 5/172
 128/DIG. 13
4,755,998 A 7/1988 Gallager
(Continued)

FOREIGN PATENT DOCUMENTS

EP 0409205 A2 1/1991

OTHER PUBLICATIONS

Bellman, Richard, "On the Approximation of Curves by Line Segments Using Dynamic Programming," Communications of the ACM, Denmark, 1961, p. 284.
(Continued)

*Primary Examiner* — Toan M Le
(74) *Attorney, Agent, or Firm* — Lewis & Reese, PLLC

(57) ABSTRACT

A de-noising algorithm is executed dynamically as data is received to generate and update a set of candidate solutions. Each candidate solution is a representation of the data using one or more line segments, and each line segment is fitted to the data within the time period that the segment spans. During each iteration of the algorithm, one candidate solution is identified as a best solution, and properties of the best solution are utilized to dynamically compute properties of the data. To limit the number of active candidate solutions and the corresponding processing power required to update and evaluate them, candidate solutions that fall too far behind the best candidate solution are eliminated from consideration. The de-noising algorithm finds particular utility in the context of a load cell signal that is representative of a weight of an intravenous fluid container.

23 Claims, 6 Drawing Sheets

(56) References Cited

U.S. PATENT DOCUMENTS 7,173,985 B1    2/2007   Diaz-Manero et al.
8,579,859 B2   11/2013   Kramer et al.

OTHER PUBLICATIONS

Bellman, Richard, et al., "Curve Fitting by Segmented Straight Lines," Journal of the American Statistical Association, vol. 64, No. 327, Sep. 1969, pp. 1079-1084.
Killick, R., et al., "Optimal Detection of Changepoints with a Linear Computational Cost," Oct. 10, 2012, pp. 1-25.
Kim, Seung-Jean, et al., "Trend Filtering," Society for Industrial and Applied Mathematics, vol. 51, No. 2, 2009, pp. 339-360.
Little, Max A., et al., "Sparse Bayesian Step-Filtering for High-Throughput Analysis of Molecular Machine Dynamics," 2010 IEEE International Conference on Acoustics Speech and Signal Processing, Mar. 2010, pp. 4162-4165.
Rigaill, Guillem, "Pruned Dynamic Programming for Optimal Multiple Change-Point Detection," Apr. 7, 2010, pp. 1-9.
Viterbi, Andrew J., "Error Bounds for Convolutional Codes and an Asymptotically Optimum Decoding Algorithm," IEEE Transactions on Information Theory, vol. IT-13, No. 2, Apr. 1967, pp. 260-269.
Yao, Yi-Ching, "Estimation of a Noisy Discrete-Time Step Function: Bayes and Empirical Bayes Approaches," The Annals of Statistics, vol. 12, No. 4, 1984, pp. 1434-1447.

\* cited by examiner

ALGORITHM FOR REMOVAL OF NOISE DURING ADMINISTRATION OF FLUID TO A PATIENT

CROSS-REFERENCE TO RELATED APPLICATIONS

This is a non-provisional of U.S. Provisional Patent Application Ser. No. 62/089,728, filed Dec. 9, 2014, which is incorporated herein by reference in its entirety, and to which priority is claimed.

STATEMENT REGARDING GOVERNMENT INTERESTS

This work was supported in part by the following United States Government grants:

| Federal Agency: | Award No.: |
| --- | --- |
| National Institutes of Health | R01HL092253 |
| Office of Naval Research | N00014-12-C-0556 |
| National Science Foundation | CNS-1040672 |

The Government may have certain rights in the invention.

NOTICE REGARDING COPYRIGHT

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present application relates to techniques for dynamically removing noise from a signal. The application may find particular utility in, and is described in the context of, the removal of noise from a load cell signal that is representative of the weight of a fluid container for accurately accounting for and displaying parameters of the administration of fluid to a patient.

BACKGROUND

Fluid therapy or the infusion of physiologic solutions into the blood of patients is a standard treatment for a variety of medical conditions including shock due to blood loss, sepsis, and burn injury. Fluid is often administered from fluid containers such as bags or bottles using mechanical pumps, hand pumps, gravity flow or pressurized sleeves that compress the fluid container. For the treatment of certain medical conditions, it is important for a caregiver to know an amount of fluids that have been administered to a patient and a timing of such fluid administration in order for a response of the patient to the fluids to be gauged, which may inform subsequent treatment activities.

One example of such a treatment is fluid resuscitation of burn shock. Following major burn injuries, the integrity of the blood vessels in the damaged tissue become leaky to fluid and plasma proteins that extravasate into the tissue spaces. This loss of vascular volume results in inadequate perfusion to vital tissues. Therefore, a standard treatment for burn-injured patients is fluid resuscitation whereby a fluid is administered to the patient at a specified rate for a specified duration (e.g., one hour). Because burn patients are at risk of under- and over-resuscitation, which can have harmful effects, it is also common practice to evaluate the patient's response to the administration of fluids (e.g., urinary output and mean arterial pressure) so that the infusion rate of fluids can be adjusted to an appropriate value.

Another example of such a treatment is the administration of fluid boluses, which are relatively large volumes of fluid administered over a short duration to hasten or magnify patient response, for the treatment of hypovolemia (decreased blood volume) and hemodynamic instability (abnormal or unstable blood pressure). Fluid boluses are typically administered at a high infusion rate for a relatively short duration to deliver a prescribed volume, and, perhaps equally as important, to enable the assessment of a patient's responsiveness to the administration of fluid. There are several direct and indirect measures of a patient's fluid responsiveness such as a defined increase in cardiac output. When the patient responds with increased cardiac output or perfusion after a fluid bolus, the caregiver can ascertain that the fluid was of benefit. However, if the patient does not respond adequately, this informs the caregiver that the patient is a non-responder and requires therapeutic measures such as cardiovascular drugs. Although the description below refers generally to intravenous (IV) fluid administration, fluid administration can also take place via interosseous (IO) and intramuscular (IM) routes.

When an IV fluid is administered by gravity feed without an infusion pump, the infusion rate is typically controlled manually by adjusting the clamping pressure on the IV infusion tube (e.g., via an adjustable thumbwheel) that connects the IV fluid container to a patient's venous catheter. To determine the infusion rate using this delivery method, a caregiver typically counts a number of drips over a given time period (e.g., one minute) to calculate and adjust the infusion rate and attempts to verify the infusion rate over a longer time period by observing a change in fluid volume in an IV fluid container, which can be highly inaccurate. When an IV fluid is administered using an infusion pump, the amount of fluid that is delivered is controlled by adjusting the infusion pump's flow setpoint. While infusion pumps allow for a more accurate control of infusion rate, they are expensive and most often fail to deliver fluid at the fast rates needed for a bolus. Because certain treatments require a precise measurement of the amount of fluid delivered and of the timing of fluid delivery, there is a need for a more accurate system and method for measuring these parameters either as a redundant measure to verify the data available from an infusion pump or as an accurate measure of fluid administration in the absence of an infusion pump.

U.S. Pat. No. 8,579,859, which is incorporated herein by reference in its entirety, describes a variety of designs of IV fluid administration systems that incorporate load cells for measuring the weight of an IV fluid bag, the change in which enables the determination of fluid administration parameters. However, the sensitive load cells that enable accurate measurements of the amount of fluid that is being administered are also susceptible to error caused, for example, by movement of the IV fluid bag, which may be exacerbated when fluids are being administered in a moving vehicle such as an ambulance or patient transport air vehicle.

While known filtering techniques significantly remove signal noise, they also reduce temporal resolution of the signal, which can be unacceptable, especially in the provision of fluid boluses in which it is desirable to identify the start and stop times of the high infusion rate period with a high degree of precision. There is therefore a need for a system and method for removing signal noise from a load cell signal for accurately determining fluid administration parameters based on weight measurements of a fluid container. In addition, there is a need for providing these determined fluid delivery parameters in real-time or near real-time and in conjunction with additional patient responsiveness parameters to provide caregivers with improved situational awareness.

DETAILED DESCRIPTION OF THE INVENTION

Figure 1:
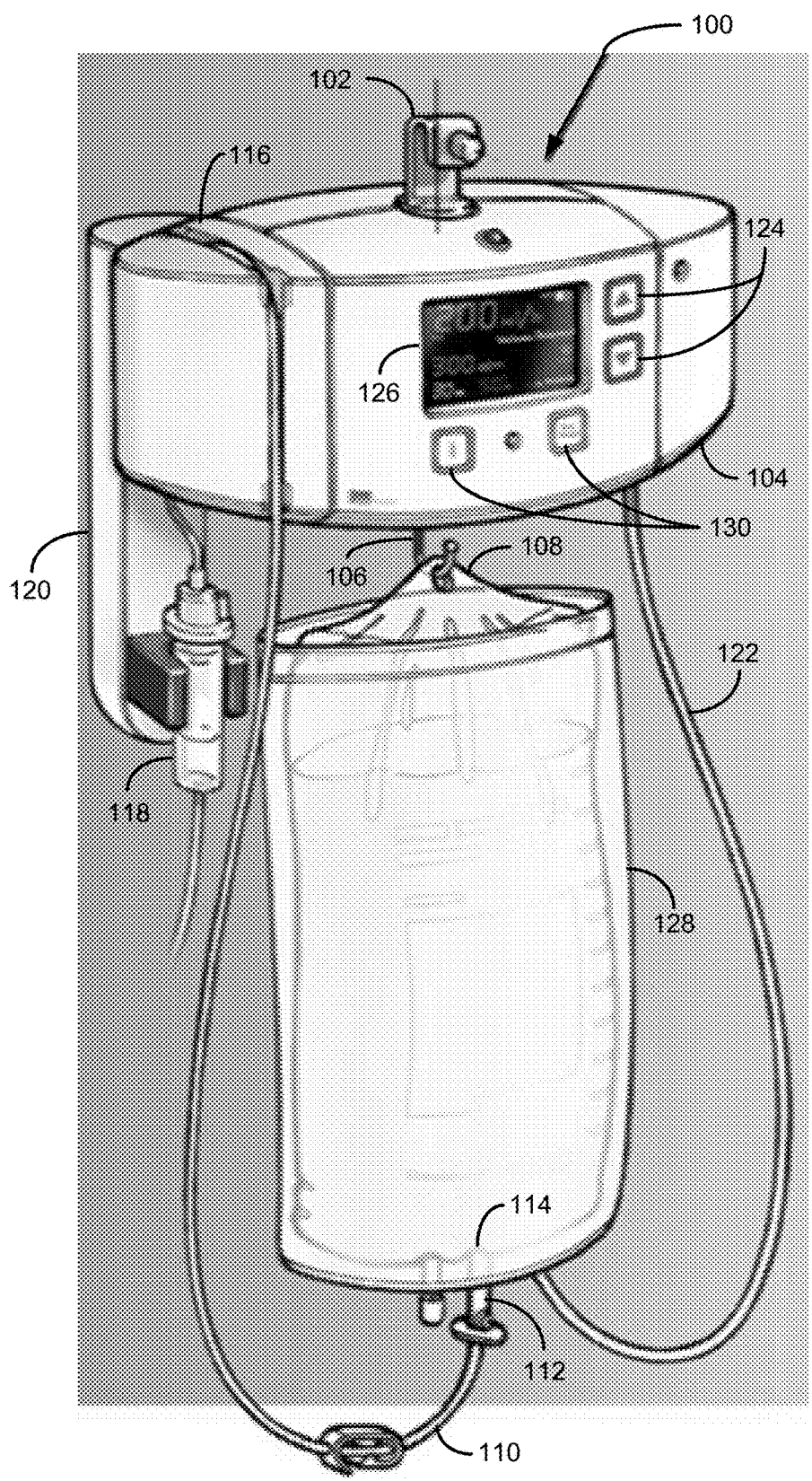
FIG. 1 shows an IV fluid administration system, in accordance with an example of the invention.

FIG. 1 illustrates an example IV fluid administration system 100 in accordance with an embodiment of the invention. The IV fluid administration system 100 includes a hanger 102 for suspending the housing 104 from a device such as an IV stand or pole. An IV fluid bag hanger 106 extends from the underside of the housing 104 and supports an IV fluid container such as the fluid bag 108. Fluid is delivered from the IV fluid bag 108 to a venous catheter inserted in a patient through tubing 110. A spike fitting 112 is coupled to one end of the tubing 110 and is inserted into an IV tubing port 114 of the bag 108 to allow fluid in the bag 108 to flow into the tubing 110. The tubing 110 is routed through a flow controller 116 that is positioned within the housing. The flow controller 116 pinches the tubing 110 to regulate the amount of fluid that is delivered from the bag 108 to the patient. From the outlet of the flow controller 116 the tubing 110 passes through a drip chamber 118 that is supported by an arm 120 connected to the housing 104. From the drip chamber 118, the tubing 110 is routed to the venous catheter inserted in the patient.

While fluid can be delivered via gravity feed or an infusion pump as described above, the driving force for fluid administration in the system 100 is a fluid bag pressurization system. The bag pressurization system includes an air compressor (situated within the housing 104) that delivers pressurized air through tubing 122 to a sleeve 128 within which the IV fluid bag 108 is positioned. The fluid bag 108 is sealed within the sleeve 128 such that the air pressure delivered to the sleeve acts on the fluid within the bag 108, causing fluid in the bag 108 to be expelled through the port 114 and into the tubing 110. The sleeve 128 can be pressurized to 300 mmHg or more, which enables the system 100 to administer fluids at a higher infusion rate than is obtainable using either gravity feed alone or standard IV infusion pumps. This is particularly valuable for the administration of fluid boluses, which, as described above, involve the administration of a prescribed volume of fluid at a relatively high infusion rate over a relatively short duration.

The system 100 includes controls 124 (i.e., buttons), which enable a caregiver to enter a desired infusion rate or bolus size. The system 100 also includes a display 126 that provides various fluid administration parameters, including current and historical infusion rate data. Parameters and data displayed could include, for example, the total volume infused, the size of an active bolus, the infusion rate, the current pressure sleeve pressure, the remaining time and volume of an active bolus, the volume and bolus duration remaining in the bag, and fluid indicators (e.g., an indicator that fluid delivery is active or a warning that the bag is close to empty and needs to be replaced). These displayed parameters may be determined in accordance with the techniques described below and may inform control actions implemented by the bag pressurization system and the flow controller 116. Controls 130 enable a caregiver to perform additional actions such as entering a fluid type and density upon changing out a fluid container, causing fluids that are not administered to a patient (e.g., to flush line 110 or to fill a syringe) to be excluded from fluid administration parameter calculations, or to change between constant infusion mode and bolus mode. While the system 100 has been illustrated and described as a fluid administration system (i.e., a system that includes a driving force for fluid delivery such as a bag pressurization system or an infusion pump), the disclosed techniques can also be implemented in a medical fluid monitor system (i.e., a system in which fluid is administered via gravity feed or via an external delivery system such as an external infusion pump).

Figure 2:
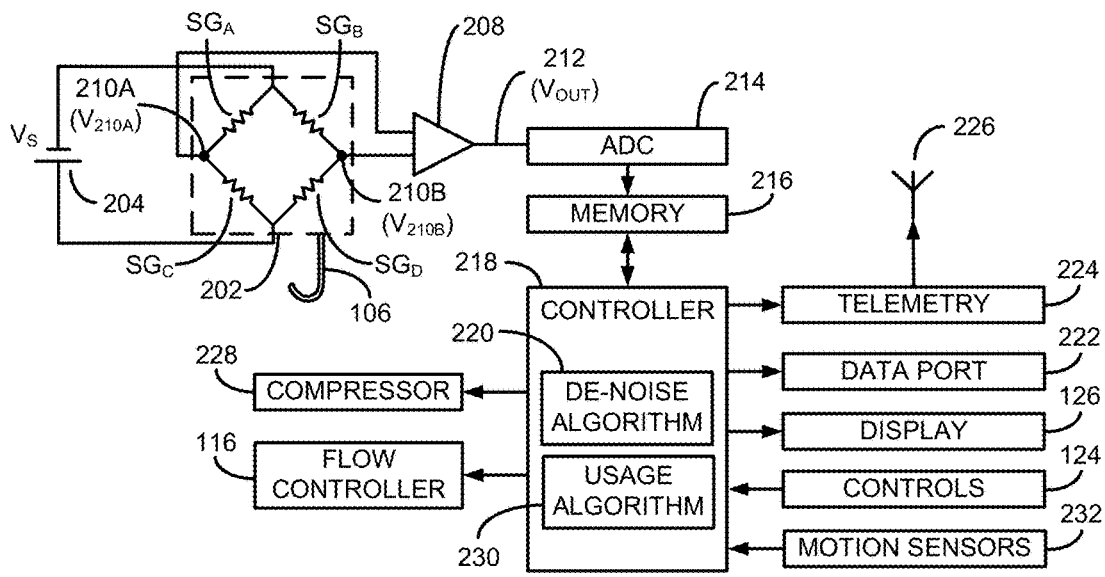
FIG. 2 shows the components of an IV fluid administration system in block diagram form, in accordance with an example of the invention.

Referring to FIG. 2, the internal components of the system 100 are shown in block diagram form. The IV bag hanger 106 is coupled to a force transducer such as load cell 202 in a way that causes the weight of the fluid container suspended from the hanger 106 to act on the load cell 202, which creates a signal that is indicative of the weight of the container. In the illustrated embodiment, a constant DC voltage ($V_S$) is supplied to the load cell 202 from a power source 204. The power source 204 may be derived from (i.e., transformed, rectified, and regulated from) an AC voltage source supplied, for example, from a wall outlet (not pictured). There are a number of different ways in which electrical components can be arranged in varying types of load cells as is known by those of skill in the art. The illustrated load cell 202 includes four strain gauges $SG_A$-$SG_D$ arranged in a Wheatstone bridge. In the absence of a force acting upon the load cell 202, the resistances of the strain gauges $SG_A$-$SG_D$ cancel out, and, as a result, there is no difference between the voltage at node 210A ($V_{210A}$) and the voltage at node 210B ($V_{210B}$) (i.e., $\Delta V=0$). However, when a force is applied to the load cell 202 the resistances of the strain gauges $SG_A$-$SG_D$ are altered, which results in a difference between the voltages $V_{210A}$ and $V_{210B}$ (i.e., $\Delta V \neq 0$) that is proportional to the force applied to the load cell. The voltage signals from the nodes 210 are supplied to an instrumentation amplifier 208 that provides a single amplified output signal 212 having a voltage $V_{OUT}$ that is proportional to the differential voltage between the input signals ($\Delta V$), and thus the weight acting upon the load cell 202. The output signal 212 is supplied to an analog-to-digital converter 214, which converts the voltage value ($V_{OUT}$) to a digital value that represents the weight of the fluid bag 108. The digital value is periodically stored in a memory 216. In one embodiment, a controller 218 (e.g., a microprocessor, a microcontroller, a FPGA, or other logic circuitry) averages digital values provided by the analog-to-digital converter (ADC) 214 over a period of 100 milliseconds to 1 second and stores the averaged value in the memory 216. Each value stored in the memory 216 includes a corresponding timestamp such that the memory includes a record of the weight of the fluid bag 108 over time. In the illustrated embodiment, the system 100 additionally includes one or more motion sensors 232, such as accelerometers, which may be positioned near load cell 202. The motion sensors 232 generate signals that are indicative of the motion of the housing 104 and of the load cell 202, in particular. This data, which is digitized, timestamped, and stored in the memory 216, can be utilized to identify an effect of motion on the signal generated by the load cell 202.

As will be described in greater detail below, the controller 218 accesses the weight data points and applies a de-noising algorithm 220 to derive fluid administration parameters such as the infusion rate as a function of time and the total volume of fluid delivered. The controller 218 also executes various usage algorithms 230, which are used in conjunction with the de-noising algorithm 220 to calculate and utilize the fluid administration parameters to provide additional alerts and computed values as described below. Certain ones of the results of the de-noising and usage algorithms are output to the display 126, to a data port 222 (such as a USB, fiber optic, or other data port), and to telemetry circuitry 224 that modulates the data for transmission via an antenna 226. An external device (e.g., a personal computer, tablet, smart phone, etc.) can receive the fluid administration parameters via a wired connection to the port 222 or wirelessly from the antenna 226. In addition to providing the parameters to the antenna 226, the data port 222, and the display 126 for logging and/or display, the parameters might also be utilized by the controller 218 to generate control signals that are provided to the flow controller 116 (e.g., a control signal to control the amount of force applied to pinch the tube 110) and to an air compressor 228 in the fluid bag pressurization system (e.g., an output air pressure to be supplied via the tubing 122 to the sleeve 128). Such control signals may be provided, for example, to adjust measured fluid administration parameters (e.g., infusion rate) towards fluid administration setpoints received at the controller 218 (e.g., an infusion rate set point entered by a caregiver using controls 124).

Figure 3A:
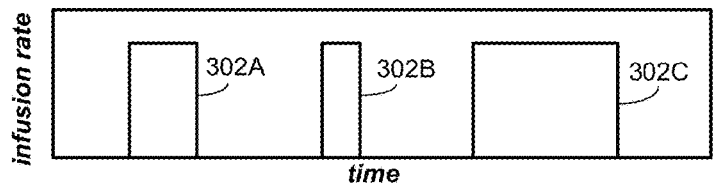
FIGS. 3A-3C show a desired IV infusion rate, corresponding expected weight data, and example measured weight data, respectively, as a function of time.
Figure 3B:
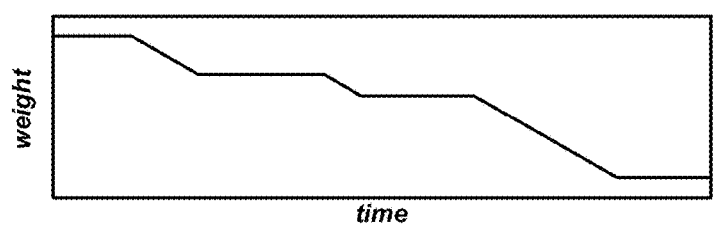
Figure 3C:
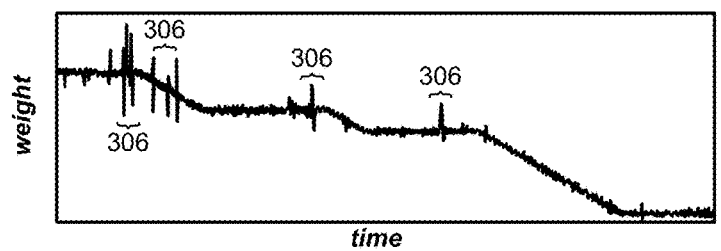

Referring to FIG. 3A, flow rate data is illustrated as a function of time for an example series of fluid boluses 302 administered using the system 100. The parameters (e.g., flow rate and duration) of the individual boluses (302A, 302B, and 302C) may be entered into the system 100 manually, as a predefined treatment regimen, or may be automatically generated by the system 100 in response to a measured patient parameter (e.g., in response to a decrease in mean arterial pressure (MAP)). FIG. 3B illustrates the expected weight and FIG. 3C illustrates example measured weight data for an IV fluid container corresponding to the administration of the desired fluid boluses 302 illustrated in FIG. 3A. It can be seen that the measured weight data generally tracks the expected weight illustrated in FIG. 3B, but it also includes a consistent low level of signal noise as well as periods of burst noise (illustrated as periods 306). The low level signal noise is generally attributable to relatively minor and persistent outside influences that affect the sensitive load cell measurements (e.g., air conditioning or ventilation system causing the IV container to swing) as well as electrical signal noise. Due to the precision required for the measurement of small changes in the volume of fluid in an IV fluid container, the load cell measurement data is susceptible to this type of persistent low-level noise. The periods of burst noise 306 are generally attributable to more significant events (e.g., movement of an IV pole or stand) that cause larger variations in the load cell measurements for a short duration. As described above, it is often necessary to understand with a high degree of precision the parameters of IV fluid administration to a patient. For example, it is desirable to understand the parameters (i.e., timing and infusion rate) associated with the administration of the fluid boluses 302. Existing methods to remove noise employ bandpass and low pass filters that successfully eliminate a large portion of the noise but that also degrade the temporal resolution of the data. For example, Savitzky-Golay filters minimize least-squares errors over fixed frames to fit a polynomial to a noisy signal. However, these filters, because they employ a fixed frame length, are unable to accurately identify a rapid change in data such as a change in weight data that marks the beginning or end of the administration of a fluid bolus. The inventors have developed de-noising algorithm 220, which overcomes the above-described deficiencies of existing processing techniques to enable an accurate determination of fluid administration parameters using weight data such as that illustrated in FIG. 3C.

Figure 4:
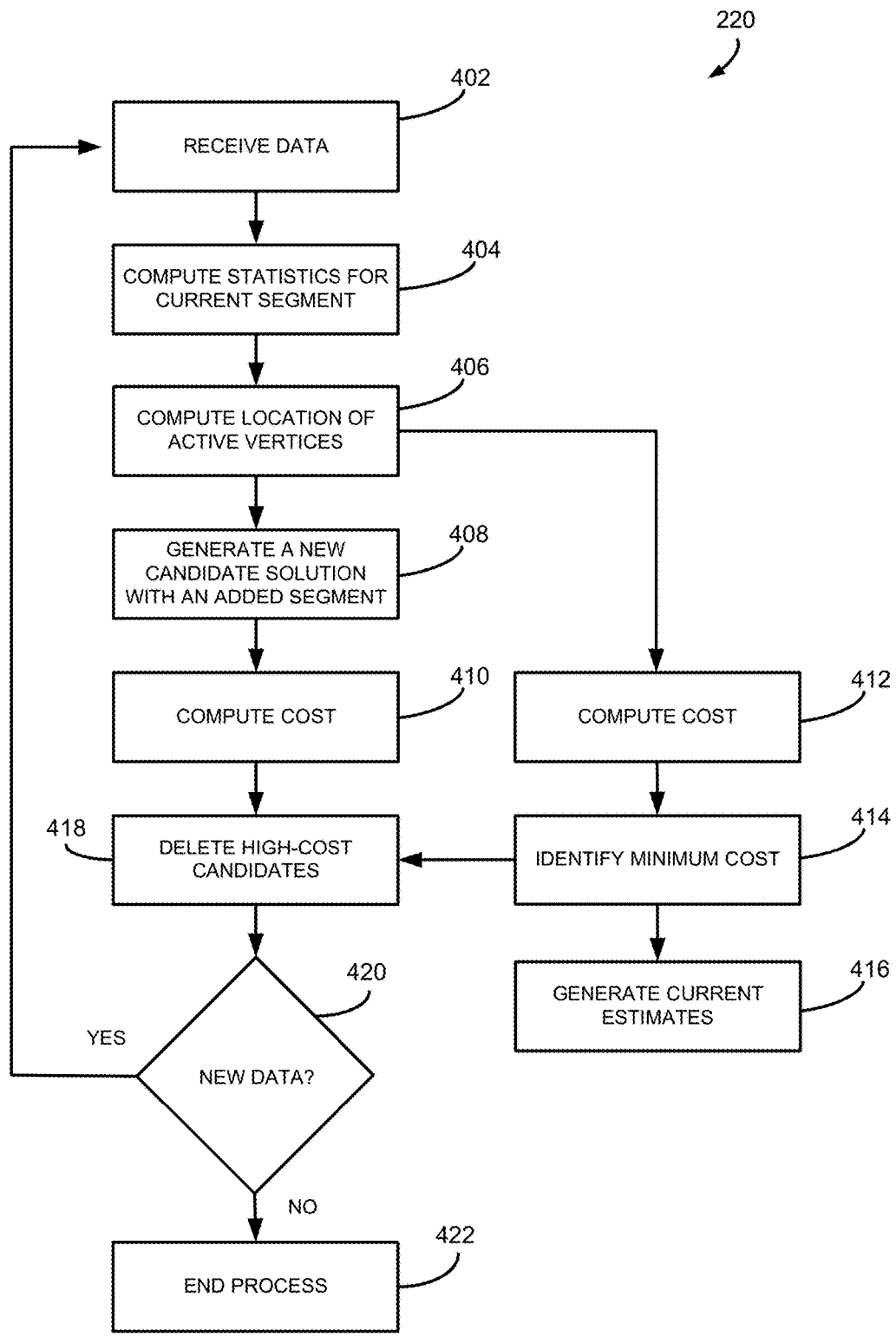
FIG. 4 shows the steps of a de-noising algorithm in flowchart form, in accordance with an example of the invention.

Before describing the algorithm 220 in detail, a brief overview is provided to introduce an overall concept and terminology. The algorithm 220 is executed dynamically as data is received (e.g., as weight measurements are obtained) to generate and update a set of candidate solutions. Each candidate solution is a representation of the data using one or more line segments, where each line segment is fitted to the data within the time period that the segment spans. As new data points are received, the positions of the vertices of active segments, which are the line segments having at least one vertex with a location that has not been fixed, are updated. During each iteration of the algorithm, one candidate solution is identified as a best solution. To limit the number of active candidate solutions and the corresponding processing power required to update and evaluate them, candidate solutions that fall too far behind the best candidate solution are eliminated from consideration. Having described the overall concept and terminology, reference is made to FIG. 4, which illustrates the steps of the de-noising algorithm 220 in flowchart form.

Figure 5A:
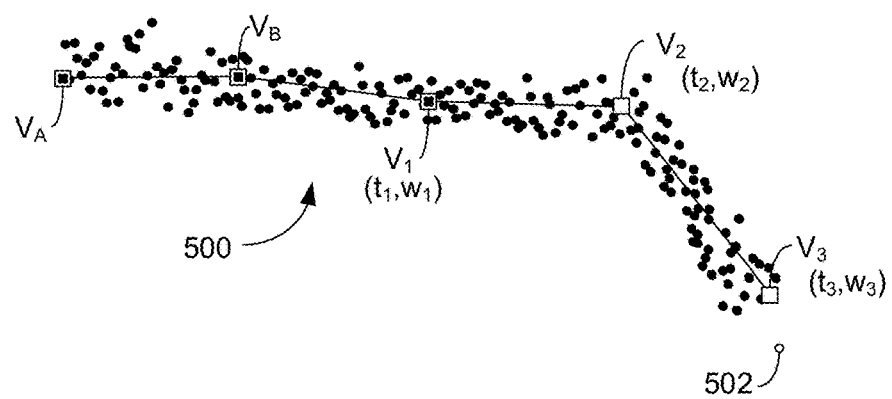
FIGS. 5A-5C show the application of various steps of the de-noising algorithm of FIG. 4 on an example data set, in accordance with an example of the invention.

Each iteration of the de-noising algorithm 220 begins with the receipt of new weight data (e.g., as weight measurements are stored in the memory 216). Upon receiving the new weight data (step 402), a set of statistics for a current line segment in each candidate solution are updated based upon properties of the newly-received data (step 404). The current segment is defined as the line segment that spans a time period that includes the time of the new data. Referring to FIG. 5A, a portion of the operation of the algorithm 220 is illustrated for a sample data set where filled circles represent previously-received data points that have been incorporated into one example candidate solution 500 and open circles represent newly-received data that has not yet been incorporated (such as data point 502), a notation that is adopted throughout this description. The current segment in the depicted example candidate solution 500 is the segment from vertex $V_2$ to vertex $V_3$, where each vertex's position is defined by a time t and a weight w.

The open squares at the vertices $V_2$ and $V_3$ indicate that the positions of these vertices have not yet been fixed.

Although the time position of the vertex $V_2$ is fixed for this particular candidate solution 500, the weight position may shift as a result of newly-received data such as data point 502. Similarly, both the time and the weight positions of the vertex $V_3$ may shift as new data is received. Conversely, the filled squares representing the vertices $V_A$, $V_B$, and $V_1$ indicate that the positions (both time and weight) of these vertices are fixed. In the illustrated example of FIG. 5A, the de-noising algorithm 220 limits the number of active segments (i.e., segments having one or more vertices that are not fixed) to the two most recent (i.e., closest in time to the present) segments. While the algorithm 220 can be configured to enable any number of segments to remain active, the inventors have observed that incoming data has very little effect on the position of vertices multiple segments in the past and that maintaining a higher number of active segments is computationally expensive. As a result, it has been determined that limiting the number of active segments to two provides accurate results and limits computational expense. The examples in this application apply this technique, and the two active segments in any candidate solution are defined as the segments from $V_1$ to $V_2$ and from $V_2$ to $V_3$. It should be noted that the positions of the vertices for any candidate solution are specific only to that candidate solution. For example, the times $t_1$, $t_2$, and $t_3$ and the weights $w_1$, $w_2$, and $w_3$ for candidate solution 500 are not necessarily the same as the corresponding parameters for another candidate solution.

Returning to FIG. 4, the statistics computed for the current segment are a sum of weights of the individual points in the segment ($N_C$), a sum of the weighted time distance of each individual point in the segment from the starting vertex ($T_C$), a sum of the weighted squared time distance of each individual point in the segment from the starting vertex ($T_C^2$), a sum of the weighted measurement values in the segment ($S_C$), a sum of the weighted squared measurement values ($S_C^2$) in the segment, and a weighted sum of cross-correlations of the individual points with time in the segment ($R_C$). These statistics are defined as follows:

$$N_C(t_2, t_3) = \sum_{i | t_2 < t_i \leq t_3} c_i$$

$$T_C(t_2, t_3) = \sum_{i | t_2 < t_i \leq t_3} c_i(t_i - t_2)$$

$$T_C^2(t_2, t_3) = \sum_{i | t_2 < t_i \leq t_3} c_i(t_i - t_2)^2$$

$$S_C(t_2, t_3) = \sum_{i | t_2 < t_i \leq t_3} c_i w_i$$

$$S_C^2(t_2, t_3) = \sum_{i | t_2 < t_i \leq t_3} c_i w_i^2$$

$$R_C(t_2, t_3) = \sum_{i | t_2 < t_i \leq t_3} c_i(t_i - t_2) w_i$$

where $w_i$ is a weight measurement captured at a time $t_i$. The term $c_i$ can be determined in different ways. In one embodiment, the $c_i$ term is universal (i.e., equal to one for every data point) such that each data point is treated equally. In another embodiment, the $c_i$ term is a weighting factor that accounts for local variance in the weight measurements within a window around the time $t_i$. In such an embodiment, the term $c_i$ can be calculated as:

$$c_k^{-1} = 1 + \frac{1}{2s+1}\left(\sum_{i=k-s}^{k+s} w_i^2\right) - \left(\frac{1}{2s+1}\sum_{i=k-s}^{k+s} w_i\right)^2$$

where k defines a position in a sliding window within which the local variance of the signal is evaluated and s defines the size of the window. In this embodiment, the weighting factor $c_i$ gives less credit to a weight measurement within a period of high local variance such as burst noise periods 306 so that such periods do not skew the properties of the segment within which such periods occur. In yet another embodiment, the $c_i$ term is determined in accordance with the output of one or more motion sensors 232 such that weight measurements recorded during periods of higher motion may be given less credit than measurements recorded during periods in which motion is low. The above statistical parameters are saved for each active segment in each candidate solution as are the time components of the starting points of all active segments (e.g., $t_1$ and $t_2$). Using the saved statistical values from the previous iteration, the statistics for the current segment can be updated recursively as:

$$N_C(t_2,t_3) = N_C(t_2,t_3)_{PRIOR} + c_{t_3}$$

$$T_C(t_2,t_3) = T_C(t_2,t_3)_{PRIOR} + c_{t_3}(t_3 - t_2)$$

$$T_C^2(t_2,t_3) = T_C^2(t_2,t_3)_{PRIOR} + c_{t_3}(t_3 - t_2)^2$$

$$S_C(t_2,t_3) = S_C(t_2,t_3)_{PRIOR} + c_{t_3} w_{t_3}$$

$$S_C^2(t_2,t_3) = S_C^2(t_2,t_3)_{PRIOR} + c_{t_3} w_{t_3}^2$$

$$R_C(t_2,t_3) = R_C(t_2,t_3)_{PRIOR} + c_{t_3}(t_3 - t_2)w_{t_3}$$

where the subscript "PRIOR" indicates the value of the statistic from the previous iteration and the subscript "$t_3$" indicates the value of the parameter for the newly-received data point. It will be noted that while these statistics are saved for active segments preceding the current segment, new data only impacts the statistics for the current segment. Therefore, statistical parameters for active segments other than the current segment are not updated.

Using the above statistics, the locations of the active vertices are calculated (step 406) for each candidate solution using the following equation:

$$\begin{bmatrix} V_{2,w} \\ V_{3,w} \end{bmatrix} = \begin{bmatrix} \frac{-2(t_2 - t_1)}{\gamma} & \frac{12}{\gamma} & \frac{12}{\gamma} & \frac{-18}{\gamma} \\ \frac{t_2 - t_1}{\gamma} & \frac{-6}{\gamma} & \frac{-6}{\gamma} & \left(\frac{9}{\gamma} + \frac{3}{t_3 - t_2}\right) \end{bmatrix} \begin{bmatrix} V_{1,w} \\ S_C(t_2, t_3) \\ \frac{R_C(t_1, t_2)}{t_2 - t_1} \\ \frac{R_C(t_2, t_3)}{t_3 - t_2} \end{bmatrix}$$

where $V_{x,w}$ represents the weight dimension value of the xth vertex and $\gamma = (t_2 - t_1) + 3(t_3 - t_1)$. The vertex location calculation is derived from the minimization of the goodness-of-fit component of the cost function, which is discussed below. Stated differently, the above vertex location calculation employs the statistical parameters to determine a pair of line segments that best fits the data over the corresponding time period and retains continuity with the preceding line segment(s).

Figure 5B:
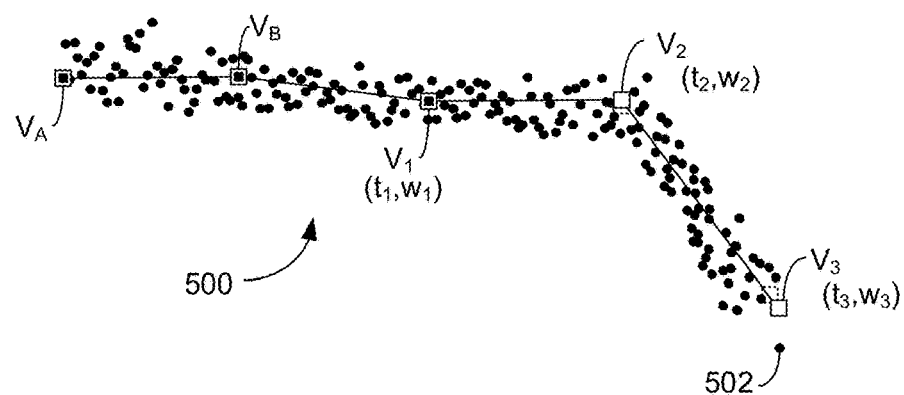

Referring to FIG. 5B, the inclusion of the data point 502 in the candidate solution 500 results in the movement of the vertex $V_3$ from the previous location (depicted as a dashed square) to the calculated location. As illustrated, the location of the vertex $V_3$ differs in both time and weight from the previous location. The time $t_3$ has shifted to match the time corresponding to the data point 502 and the weight has shifted to accommodate the data between $V_2$ and $V_3$, which now includes data point 502. The change in the location of the vertex $V_3$ also affects the location of the vertex $V_2$, which has a fixed time position $t_2$ but a floating weight position that is defined as the point at which the current segment intersects $V_2$.

Figure 5C:
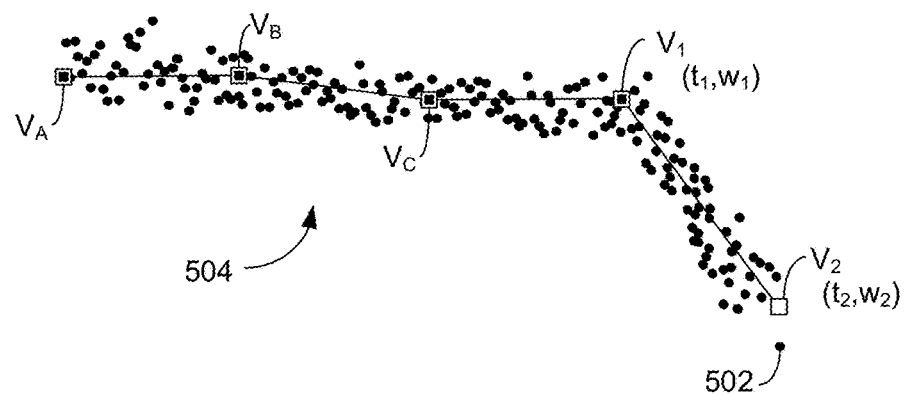

After calculating the locations of the active vertices, for each candidate solution, a new candidate solution is generated in which the calculated endpoint vertex of the current segment becomes the starting vertex for a new segment (step 408). For example, referring to FIG. 5C, a new candidate solution 504 is created from the candidate solution 500. In the new candidate solution 504, the calculated location of the endpoint vertex of the current segment becomes the starting vertex for a new current segment. The location of the vertex $V_2$ in candidate solution 500 becomes a fixed location of vertex $V_1$ in the candidate solution 504. Similarly, the location of the vertex $V_3$ in candidate solution becomes the location of the vertex $V_2$ (which is fixed in time but not weight as described above) in the candidate solution 504.

After the new candidate solutions are created, the cost of each candidate solution is determined (steps 410 and 412). Tracking the cost of the candidate solutions serves two functions. First, it enables the current best (i.e., lowest cost) candidate solution to be determined for use in dynamically calculating fluid administration parameters such as infusion rate. Second, it allows for the elimination of non-viable candidate solutions, which must be eliminated because the generation of a new candidate solution for each existing candidate solution in each iteration of the algorithm 220 results in an exponential growth in the number of candidate solutions.

The cost is made up of two components: a component that accounts for the goodness-of-fit of the segments to the measured data and a component that accounts for the complexity of the candidate solution. It will be understood that there is a tradeoff between these components. For example, a candidate solution having nearly as many segments as data points would almost perfectly fit the data, but it would be essentially no less noisy than the data itself. As a result, the cost function seeks to strike a balance between complexity and goodness-of-fit.

The goodness-of-fit component may be computed using known data fitting statistics. For example, the fit component may be computed as an integral-square residual error as:

$$A = \sum_{t_0}^{t_3} c_i(x_i - w_i)^2$$

where $x_i$ is the segment value of the candidate solution at a time $t_i$ at which a weight measurement $w_i$ is recorded and $t_0$ is the time corresponding to the first data point in the data set. The complexity component is equivalent or proportional to the number of vertices in the candidate solution. The total cost is defined as:

$$C = A + \delta B$$

where C is the total cost of a candidate solution, B is the complexity component, and $\delta$ is a tuning vertex penalty parameter that controls a tradeoff between the complexity and fit components. The product of the penalty, $\delta$, and the complexity cost, B, is the weighted complexity cost. The vertex penalty, $\delta$, must be determined for the type of data being evaluated. Factors that influence the selection of the vertex penalty parameter include data sampling rate, measurement noise power, and specific gravity of the fluid being administered.

The cost of each candidate solution for the non-active segments (e.g., the segments from $t_0$ to $t_1$) is maintained in memory as a parameter of the candidate solution along with the statistics and times described above. Given the saved cost of the non-active segments for each candidate solution, the cost for the active segments (e.g., from $t_1$ to $t_3$) can be computed and added to the saved cost to obtain the total candidate solution cost. The goodness-of-fit cost of the active segments can be computed from the above statistical parameters as:

$$A = S_C^2(t_1, t_2) + S_C^2(t_2, t_3) + V^T \begin{bmatrix} t_2 - t_1 & 0 & 0 \\ t_2 - t_1 & t_3 - t_1 & t_3 - t_2 \\ 0 & 0 & t_3 - t_2 \end{bmatrix} \frac{V}{3} - V^T \begin{bmatrix} 2 & 0 & -2 & 0 \\ 0 & 2 & 2 & -2 \\ 0 & 0 & 0 & 2 \end{bmatrix} \begin{bmatrix} S_C(t_1, t_2) \\ S_C(t_2, t_3) \\ R_C(t_1, t_2) \\ t_2 - t_1 \\ R_C(t_2, t_3) \\ t_3 - t_2 \end{bmatrix}$$

where V is the matrix $$\begin{bmatrix} V_{1,w} \\ V_{2,w} \\ V_{3,w} \end{bmatrix}.$$

The goodness-of-fit cost can then be added to the weighted complexity cost, which is a function of the number of vertices in the active segments, to obtain the total cost of the candidate solution.

Having calculated the costs of the active candidate solutions, the candidate solution having the minimum cost is determined (step 414). Because the addition of a new segment (i.e., an additional vertex) increases cost, the minimum cost candidate solution will necessarily come from the set of candidate solutions for which a new segment was not added during the current iteration (i.e., none of the candidate solutions created in step 408 can be the minimum cost solution during the current iteration). As a result, only the costs for the set of candidate solutions that existed at the start of the current iteration need to be evaluated to determine the minimum cost solution.

Figure 6A:
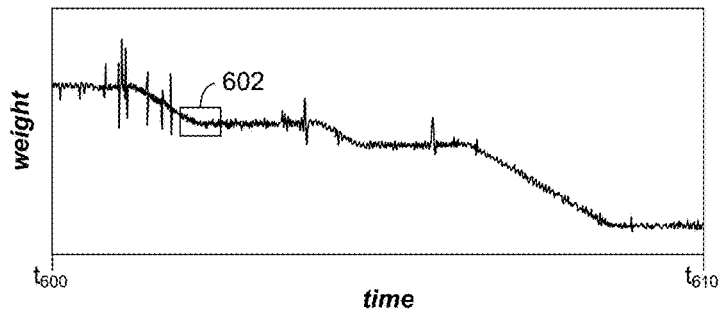
FIG. 6A shows an example data set and FIGS. 6B-6D show results of the operation of the de-noising algorithm of FIG. 4 on the example data set at different times, in accordance with an example of the invention.
Figure 6B:
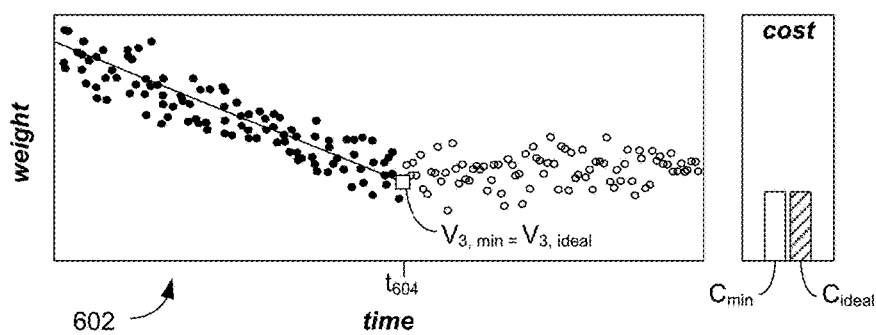
Figure 6C:
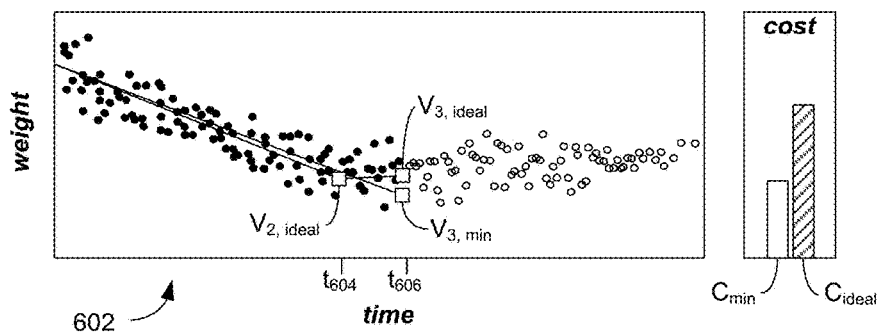
Figure 6D:
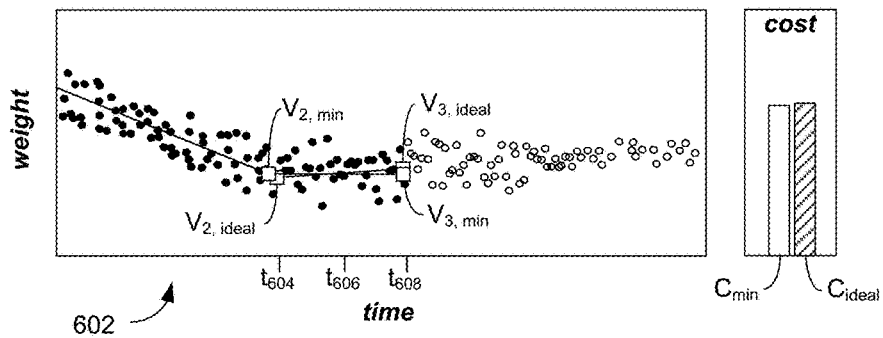

FIGS. 6A-6D illustrate the identification of the minimum-cost candidate solution as new data points are received. FIG. 6A illustrates a complete set of weight data points that are collected over a time period from $t_{600}$ to $t_{610}$. FIGS. 6B-6D show data points within a sliding window 602 as new data points are received between time $t_{604}$ and time $t_{608}$. Each of FIGS. 6B-6D shows the location of vertices and the current cost associated with an eventual ideal candidate solution and a current minimum-cost candidate solution. The eventual ideal candidate solution is the candidate solution that is eventually identified as the candidate solution having the minimum cost after the full set of data points between $t_{600}$ and $t_{610}$ has been evaluated and its corresponding parameters are labeled with the subscript "ideal." The current minimum-cost candidate solution is the candidate solution having the minimum cost at the time associated with each of the FIGS.

6B-6D (i.e., $t_{604}$ for FIG. 6B., $t_{606}$ for FIG. 6C, etc.) and its corresponding parameters are labeled with the subscript "min." In each of FIGS. 6B-6D, data points illustrated as filled circles have already been received and are included in the computation of the candidate solutions while open circles occur in the future (from the time perspective corresponding to each particular figure) and are not included in the computation of the candidate solutions.

As can be seen from the illustration of the full data set in FIG. 6A, the sliding window 602 in each of the FIGS. 6B-6D spans a period during which the data points illustrate a change in infusion rate (e.g., the end of a fluid bolus). In FIG. 6B, the ideal candidate solution is also the current minimum-cost solution. As a result, the location of the vertex $V_{3,\ ideal}$ is also the location of the vertex $V_{3,\ min}$, and the cost $C_{ideal}$ is equal to the cost $C_{min}$. Turning to FIG. 6C, the ideal candidate solution includes a vertex $V_{2,\ ideal}$ at approximately time $t_{604}$ while the current minimum-cost candidate solution does not include a corresponding additional vertex but instead continues its current segment. Due to the infusion rate transition near time $t_{604}$, the data points reflect a relatively constant weight between time $t_{604}$ and $t_{606}$ as opposed to the decreasing weight indicated by the data points before $t_{604}$. As a result, the current segment of the ideal candidate solution (i.e., the segment from $V_{2,\ ideal}$ to $V_{3,\ ideal}$), which tracks the data between $t_{604}$ and $t_{606}$, diverges from the current segment of the current minimum-cost candidate solution, which continues the general decreasing-weight trajectory indicated by the data points preceding time $t_{604}$. While the ideal candidate solution more accurately fits the data, it is penalized for the addition of a vertex and is therefore not the minimum-cost solution at time $t_{606}$. This is illustrated in the cost chart, which shows $C_{ideal}$ to be significantly greater than $C_{min}$. Turning to FIG. 6D, at time $t_{608}$, both the ideal candidate solution and the minimum-cost candidate solution account for the transition in flow rate by identifying vertices $V_2$ near time $t_{604}$. At this point, the penalty for the additional vertex has been offset by the increased accuracy with which both the ideal and minimum-cost candidate solutions fit the data. Although both the minimum-cost candidate solution and the ideal candidate solution have an equal complexity cost (i.e., both include the same number of segments), the minimum-cost candidate solution, which includes a vertex $V_{2,\ min}$ which slightly precedes in time the location of the ideal candidate solution's vertex $V_{2,\ ideal}$, is determined to more accurately fit the data at the time $t_{608}$. As a result, the cost $C_{ideal}$ is slightly greater than the cost $C_{min}$.

Returning to FIG. 4, the properties of the minimum-cost candidate solution at any point in time are utilized to provide a dynamic estimate of fluid administration parameters (step 416). These fluid administration parameters include volumetric flow rate and total fluid volume delivered, which are calculated as:

$$\dot{V} = \left(\frac{w_{t_3} - w_{t_2}}{t_3 - t_2}\right)\rho^{-1}$$

$$V = (w_{t_3} - w_{t_0})\rho^{-1}$$

where V is the total volume of fluid administered since the beginning of the weight data set, $\dot{V}$ is the current volumetric flow rate, $\rho$ is the fluid density, and the weight and time properties are those calculated for the current minimum-cost candidate solution. While the above equations assume certain time periods for the infusion rate (i.e., the infusion rate is computed based on properties of the current segment of the minimum-cost candidate solution) and volume (i.e., calculated over the full time of the data set) calculations, different times can also be utilized as will be recognized by those skilled in the art. Moreover, the fluid administration parameters may also be computed directly in mass units without the incorporation of a density term.

It will be recognized from the description of FIGS. 6A-6D that the cost penalty associated with the identification of a transition point results in a delay in recognizing the best candidate solution as the minimum-cost solution. For this reason, in one embodiment, an intentional delay may be introduced into calculation of fluid administration parameters. For example, in such an embodiment, the algorithm 220 may utilize properties of a current minimum-cost candidate solution to calculate fluid administration parameters which held in the recent past (i.e., after the passing of a certain amount of time or the receipt of a certain number of data points).

In one embodiment, one of the usage algorithms 230 enables a caregiver to input fluid type and associated fluid density (e.g., a normal saline IV solution with a measured density of 1.0046 g/mL). In another embodiment, one of the usage algorithms 230 computes a likelihood that a sharp increase in weight represents an IV fluid container change, and, when the likelihood exceeds a certain threshold, prompts a caregiver to confirm that the weight change corresponds to the administration of a new fluid and to enter the fluid type and the volume of fluid in the fluid container (e.g., lactated Ringers in 500 mL bag). Such algorithms may automatically re-initialize the weight data set (i.e., reset time $t_0$) upon the observance of a sharp increase in weight or may prompt a user to confirm that this is a desired approach. In addition to the total volume delivered since the beginning of the weight data set (i.e., since $t_0$), various ones of the usage algorithms 230 also compute the total volume of fluid delivered over certain predetermined time intervals in a similar manner. For example, the total volume of fluid delivered over the prior 10 minutes, 30 minutes, 1 hour, 4 hours, and 8 hours may be calculated.

Although not illustrated in FIG. 2, the controller 218 may also measure and/or receive additional data and various ones of the usage algorithms 230 may utilize such data in conjunction with the fluid administration parameters to compute additional parameters of interest. For example, the system 100 may also measure or receive inputs indicative of certain physiological conditions of a patient (e.g., mean arterial pressure, arterial oxygen saturation, cardiac output pulse pressure variability, etc.). Using the calculated fluid administration parameters in conjunction with the physiological data, a usage algorithm 230 can compute values that are indicative of the effectiveness of the administration of fluids. For example, such an algorithm may automatically identify the administration of a fluid bolus as a sudden increase in the flow rate and may compute the percent change in a particular physiological condition at specified time periods following the administration of the fluid bolus. The computed fluid effectiveness parameters can be utilized to adjust the administration of fluids (e.g., to continue or discontinue the administration of fluid boluses).

Additional ones of the usage algorithms 230 may also utilize the fluid administration data to compute the likelihood of an event such as an occlusion, a leak, or air in the tubing and to alert a caregiver when a likelihood of such an event exceeds a certain threshold. For example, if the measured infusion rate deviates from an infusion rate setpoint by ±10%, the controller 218 may generate an alert.

Certain ones of the usage algorithms 230 may also utilize the fluid administration parameters to predict the occurrence of future events such as the time at which a fluid bag 108 will be emptied or the time at which a current fluid bolus having a specified volume will be complete.

Usage algorithms 230 are also utilized to control fluid administration. For example, when the measured infusion rate deviates from an infusion rate setpoint, the controller 218 provides a control output to either or both of the air compressor 228 and the flow controller 116 to adjust the infusion rate towards the setpoint. In one embodiment, one of the usage algorithms 230 is a proportional-integral-derivative (PID) control algorithm executed by the controller 218 to control fluid administration to a setpoint value. In other embodiments the usage algorithms 230 could include a fuzzy logic control algorithm or a decision table control algorithm.

Figure 7:
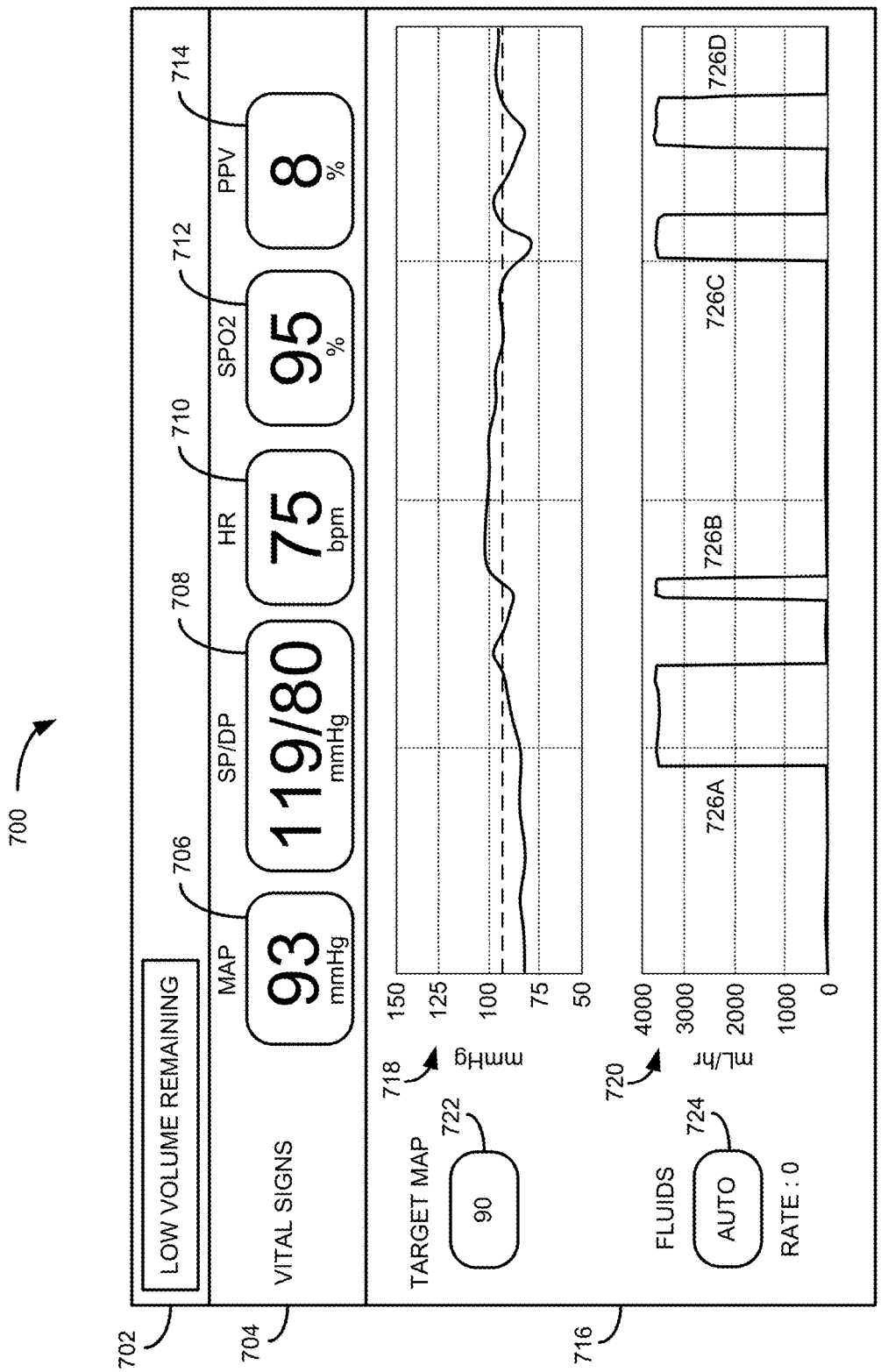
FIG. 7 shows a patient status graphic, in accordance with an example of the invention.

Referring to FIG. 7, certain ones of the fluid administration parameters as well as the outputs of usage algorithms 230 are incorporated in an example graphic 700 that presents such parameters in conjunction with additional physiological data to provide improved situational awareness to caregivers that are often overwhelmed with other treatment activities. The graphic 700 may be provided via the display 126 or on an external device connected to the system 100 through a wired connection to the data port 222 or through a wireless connection via antenna 226. The graphic 700 includes an alarm bar 702 within which abnormal conditions such as the deviation of a measured infusion rate from a setpoint, a detected low container volume, or a mean arterial pressure outside of a desired range may be displayed. The graphic 700 also includes a vital signs panel section 704. The vital signs panel 704 includes displays for the current values of a patient's mean arterial pressure 706, blood pressure 708, heart rate 710, arterial oxygen saturation 712, and pulse pressure variability 714. The graphic 700 additionally includes a historical section 716, which displays the patient's mean arterial pressure on a chart 718 and IV fluid infusion rate on a chart 720, each as a function of time. The infusion rate values indicated on the chart 720 are calculated in accordance with the algorithm 220 described above. As illustrated, the de-noising algorithm converts noisy weight data to a sharp and precise representation of fluid infusion rate. The graphic 700 additionally includes an interface 722 through which a caregiver can provide a target mean arterial pressure value as well as an interface 724 through which the caregiver can set a fluid administration mode of operation. In the automatic fluid administration mode illustrated in graphic 700, the administration of fluids is controlled automatically by the system 100. For example, as illustrated, when the measured mean arterial pressure decreases below the entered target value, fluid boluses 726 are administered automatically.

Having illustrated the utility of the current minimum-cost candidate solution in the generation of dynamic fluid administration and related data, reference is again made to FIG. 4. In addition to being utilized to provide fluid administration and related data, the minimum-cost candidate solution is also utilized as the standard according to which other candidate solutions are evaluated. After the minimum-cost candidate solution is determined, non-viable candidate solutions are deleted (step 418). Candidate solutions having a cost that exceeds a cost threshold are deleted. In one embodiment, the cost threshold is computed as a function of the minimum cost. For example, all candidate solutions having a cost that exceeds the minimum cost by a certain threshold may be eliminated. In one embodiment, all candidate solutions that exceed the minimum cost by $2\delta$ are eliminated, where $\delta$ is the vertex penalty parameter described above.

In addition to the elimination of non-viable candidate solutions as a function of their costs, the number of active candidate solutions can also be controlled by limiting the creation of new candidate solutions. In one embodiment, new candidate solutions may not be generated from all existing candidate solutions. For example, at step 408 new candidate solutions may only be generated from existing candidate solutions that have a cost that is within a certain percentage of the minimum cost (e.g., only those candidate solutions having a cost that is less than the minimum cost plus $1.2\delta$). Similarly, new candidate solutions may only be generated for a certain portion of the existing candidate solutions (e.g., only the 20% of the existing candidate solutions having the lowest costs) with the limitation that a new candidate solution must be generated from at least one candidate solution for each iteration. In one implementation, a new candidate solution is only created from the minimum-cost candidate solution. It has been observed that the number of candidate solutions generally grows during periods in which the weight data has a relatively constant slope (e.g., periods where no fluid is being administered or periods where fluid is being administered at a constant rate); however, when the weight data indicates an actual transition (e.g., a transition from one fluid infusion rate to another), the number of candidate solutions decreases rapidly as the goodness-of-fit component of the cost function increases for those candidate solutions that continue the current segment and only the candidate solutions in which a new segment is started near the transition point survive the cost analysis.

After the non-viable candidate solutions are deleted, it is determined if any additional data measurements should be recorded (step 420). If an additional data point measurement is to be recorded (the "Yes" prong of step 420), the new data point is received (step 402) and the next iteration of the algorithm 220 is performed to incorporate the new data. If no additional data is being recorded (i.e., the data set is complete) (the "No" prong of step 420), execution of the algorithm 220 is halted (step 422) and the minimum-cost candidate solution is recorded to memory 216 as the ideal candidate solution. In one embodiment, the ideal candidate solution computed when the data set is complete is stored to an electronic medical record.

As illustrated above, the disclosed de-noising algorithm 220 provides an accurate dynamic estimation of properties of a noisy data set. While the above description has focused on the implementation of the algorithm in the context of fluid administration using noisy weight data, it will be understood that the algorithm can be implemented to provide similar results for other types of data. Additional details regarding the derivation of certain portions of the disclosed de-noising algorithm are provided in U.S. Provisional Patent Application Ser. No. 62/089,728, which is incorporated herein and from which this application claims priority.

While the invention herein disclosed has been described in terms of specific embodiments and applications thereof, numerous modifications and variations could be made thereto by those skilled in the art without departing from the scope of the invention set forth in the claims.

What is claimed is:

1. A medical fluid monitor system, comprising:
a hanger configured to suspend a container of a fluid to be intravenously administered to a patient;

a force transducer coupled to the hanger and configured to generate a signal that is proportional to a weight of the fluid in the container;

a display configured to present one or more fluid administration parameters indicative of the fluid intravenously administered to a patient; and a controller configured to execute logic to iteratively:
receive a value corresponding to the signal;
update each of a plurality of candidate solutions based on the received value, wherein each candidate solution is a representation, comprised of one or more line segments, of a set of values corresponding to the signal at previous times;
generate one or more additional candidate solutions to be included in the plurality of candidate solutions;
determine a cost of each of the plurality of candidate solutions;
eliminate candidate solutions having a cost that exceeds a cost threshold;
compute one or more fluid administration parameters based on a first candidate solution, wherein the first candidate solution is selected based on its cost; and
present the one or more fluid administration parameters via the display.

2. The medical fluid monitor system of claim 1, wherein the logic to update each of the plurality of candidate solutions comprises logic to update a location of one or more vertices of each active segment in each of the plurality of candidate solutions.

3. The medical fluid monitor system of claim 2, wherein the logic to update the location of one or more vertices of each active segment in each of the plurality of candidate solutions comprises logic to incorporate the received value into each of a plurality of statistical metrics of a current segment in each of the plurality of candidate solutions.

4. The medical fluid monitor system of claim 3, wherein the logic to incorporate the received value into each of a plurality of statistical metrics comprises logic to incorporate the received value using a recursive computation and a stored value of each of the plurality of statistical metrics from a previous iteration.

5. The medical fluid monitor system of claim 2, wherein the logic limits a number of active segments within each candidate solution.

6. The medical fluid monitor system of claim 5, wherein the number of active segments in each candidate solution is limited to two.

7. The medical fluid monitor system of claim 1, wherein the logic to generate one or more additional candidate solutions comprises logic to generate the one or more additional candidate solutions by adapting an existing candidate solution to incorporate a new line segment that begins at a time associated with the received value.

8. The medical fluid monitor system of claim 1, wherein the logic to determine a cost of each of the plurality of candidate solutions comprises logic to determine a cost as a function of both a goodness-of-fit metric and a complexity metric of each candidate solution.

9. The medical fluid monitor system of claim 8, wherein the complexity metric is proportional to a number of vertices in a candidate solution.

10. The medical fluid monitor system of claim 1, wherein the first candidate solution is the one of the plurality of candidate solutions having a minimum cost.

11. The medical fluid monitor system of claim 10, wherein the logic to generate one or more additional candidate solutions comprises logic to generate one or more additional candidate solutions from existing candidate solutions that have a cost within a specified range of the minimum cost.

12. The medical fluid monitor system of claim 10, wherein the cost threshold is determined as a function of the minimum cost.

13. The medical fluid monitor system of claim 1, wherein the one or more fluid administration parameters of the medical fluid monitor system include a likelihood of a bag change, an occlusion, or a leak.

14. The medical fluid monitor system of claim 1, wherein some or all of the one or more fluid administration parameters are computed after a time delay.

15. The medical fluid monitor system of claim 1, wherein the one or more fluid administration parameters of the medical fluid monitor system comprise a fluid infusion rate.

16. The medical fluid monitor system of claim 1, wherein the controller further receives or measures one or more physiological conditions of a patient and presents the one or more physiological conditions via the display.

17. The medical fluid monitor system of claim 16, wherein the system uses the one or more physiological conditions to determine fluid effectiveness to adjust an administration of fluids.

18. A method of administering a fluid to a patient using a force transducer signal representative of a weight of the fluid, comprising iteratively:
receiving a representation of the force transducer signal;
updating each of a plurality of candidate solutions based on the received representation, wherein each candidate solution is a representation, comprised of one or more line segments, of a set of representations of the signal at previous times;
generating one or more additional candidate solutions to be included in the plurality of candidate solutions;
determining a cost of each of the plurality of candidate solutions;
eliminating candidate solutions having a cost that exceeds a cost threshold;
computing one or more fluid administration parameters based on a first candidate solution, wherein the first candidate solution is selected based on its cost; and
adjusting an administration of the fluid to the patient based on the one or more fluid administration parameters.

19. The method of claim 18, wherein the act of generating one or more additional candidate solutions comprises generating the one or more additional candidate solutions by adapting an existing candidate solution to incorporate a new line segment that begins at a time associated with the received representation.

20. The method of claim 18, wherein the act of determining a cost of each of the plurality of candidate solutions comprises summing a goodness-of-fit cost and a weighted complexity cost for each of the plurality of candidate solutions.

21. The method of claim 18, wherein updating each of the plurality of candidate solutions comprises updating a location of one or more vertices of each active segment in each of the plurality of candidate solutions.

22. The method of claim 21, wherein updating the location of one or more vertices of each active segment in each of the plurality of candidate solutions comprises incorporating the received value into each of a plurality of statistical metrics of a current segment in each of the plurality of candidate solutions.

23. The method of claim 18, wherein one of the one or more fluid administration parameters comprises a fluid infusion rate or a fluid volume.

\* \* \* \* \*